United States Patent [19]
Peel et al.

[11] Patent Number: 5,710,124
[45] Date of Patent: Jan. 20, 1998

[54] METHOD FOR COMBATTING BOVINE MASTITIS

[75] Inventors: John Edmondson Peel, Lully; Bruno Suri, Bubendorf, both of Switzerland

[73] Assignee: Novartis Corporation, Summit, N.J.

[21] Appl. No.: 596,203

[22] PCT Filed: Aug. 3, 1994

[86] PCT No.: PCT/EP94/02567

§ 371 Date: Feb. 16, 1996

§ 102(e) Date: Feb. 16, 1996

[87] PCT Pub. No.: WO95/05844

PCT Pub. Date: Mar. 2, 1995

[30] Foreign Application Priority Data

Aug. 20, 1993 [EP] European Pat. Off. ............ 93810588

[51] Int. Cl.⁶ .................................................. A61K 38/00
[52] U.S. Cl. ............................................ 514/2; 514/12
[58] Field of Search ............................................ 514/2, 12

[56] References Cited

U.S. PATENT DOCUMENTS

| | | | |
|---|---|---|---|
| 4,980,163 | 12/1990 | Blackburn et al. | 424/94.63 |
| 5,304,540 | 4/1994 | Blackburn et al. | 514/2 |
| 5,334,582 | 8/1994 | Blackburn et al. | 514/2 |

FOREIGN PATENT DOCUMENTS

| | | |
|---|---|---|
| 0181578 | 5/1986 | European Pat. Off. |
| 0342486 | 11/1989 | European Pat. Off. |
| B-10342486 | 11/1989 | European Pat. Off. |
| B-10-359873 | 3/1990 | European Pat. Off. |
| 9009739 | 9/1990 | WIPO |
| 91/07164 | 5/1991 | WIPO |
| 9313793 | 7/1993 | WIPO |

OTHER PUBLICATIONS

Journal of Dairy Science, vol. 74., #SP. 1, p. 204 (1991), P.M. Sears et al.
Journal of Dairy Science, vol. 74, #SP. 1, p. 203 (1991), P.M. Sears et. al.
Cab International, 88: 30552 Caba (1988).
Jung, et al., J. Dairy Sci 75, pp. 387–393 (1992).
Cullor et al., "Disorders of the Mammary Gland in Large Animal Medicine", ed. B P Smith, The CV Mosby Co., St. Louis, Missouri 63146, pp. 1047–1067.
Hogan et al. J. Dairy Sci 73: 2580–2585 (1990).
Philpot, Nelson W. "Economics of Mastitis Control": in: Veterinary Clinics of N. America: Large Animal Practice 6(2), pp. 233–245 (1984).
Schnell et al., FEMS Microbiol Lett 58, pp. 263–268 (1989).
Fiedler et al., Chromatographia 26, pp. 215–220 (1988).
Siegmund et al., *The Merck Veterinary Manual*, 5th Ed. (1979) pp. 840 and 841.

*Primary Examiner*—Kevin E. Weddington
*Attorney, Agent, or Firm*—Edward McC. Roberts

[57] ABSTRACT

A method for treating or preventing mastitis in cows is disclosed. The method contemplates the intramammary injection or dipping the teat with Gallidermin and/or Epidermin or one of their pharmaceutically acceptable acid salts. Gallidermin and/or Epidermin or one of their pharmaceutically acceptable acid salts can be administered prior to infection to effectively suppress the rate, severity, and duration of subsequent bacterial infection, or can be administered subsequent to infection to effectively treat mastitis.

8 Claims, No Drawings

METHOD FOR COMBATTING BOVINE MASTITIS

The present invention relates to the use of Gallidermin and Epidermin or a pharmaceutically acceptable acid addition salt thereof in the prevention and treatment of bovine mastitis. In particular, the invention relates to the use of Gallidermin and Epidermin or of a pharmaceutically acceptable acid addition salt thereof for the preparation of a pharmaceutical for the prevention and treatment of bovine mastitis (anti-mastitis drug). Teat dipping drugs are included.

Mastitis is an inflammatory disease of the mammalian mammary gland. In veterinary medicine the most important and the most frequently encountered mastitis is that of dairy cows.

Dairy cattle are highly specialised for milk production. They produce much more milk than is needed to nourish a calf. This super production, and the convention of milking dairy cows 2 or at most 3 times during 24 hours, renders their mammary glands susceptible to bacterial infections. In addition, they are milked by a mechanical apparatus that passes from cow to cow and so infection is transmitted from one animal to another.

The mammary gland has a number of natural defense mechanisms against bacterial pathogens (Cullor et al., 1990). These can be overcome by high levels of bacterial challenge and also by compromise of these defense mechanisms. This compromise can be brought about by poor management or through physiological changes at certain times in the lactation cycle (Cullor et al., 1990).The period around drying off and calving are associated with a relatively high incidence of mastitis.

Mastitis can be caused by many different species of bacteria. Those most commonly implicated in bovine mastitis fall into 2 categories I and II: Category I embraces host pathogens such as *Staphylococcus aureus* and *Streptococcus agalactiae*. These live on the skin of the udder or in the udder and individual cows are the source of infection to others in the herd. Category II embraces environmental pathogens such as *Streptococcus uberis* and *Escherichia coli*. As their name suggests these category II bacteria are found in the immediate environment of the dairy cow and so present a constant risk (Cullor et al., 1990).

Mastitis caused by the bacteria characterized above can manifest as either clinical or subclinical disease (Cullor et al., 1990). Clinical disease can vary from mildly affected quarters with changes in the milk through severely infected quarters with eventual loss of that quarter, to a systemically ill cow that may die. Milder presentations are more usual.

Subclinical mastitis as its name suggests is not obviously present. It is, however, very prevalent in many dairy herds. Subclinically affected quarters have bacteria present and the cell content of milk is greater than normal. This syndrome is accompanied by lower production. Indeed, it has been estimated that up to 70% of the economic losses sustained by farmers because of mastitis can be attributed to lost production from subclinical disease (Philpot, W. N., 1984).

Currently mastitis is controlled through the exercise of scrupulous hygiene at milking, by detection of chronic subclinically infected cows and either milking them after the non infected cows or even by eliminating them from the herd. Clinical cases are generally treated with antibiotics as they occur such as, for example, those given in Table 4. This means that milk must be withheld from sale for about 4 to 8 milkings and consequently causes economic loss to the farmer. Antimicrobial therapy of subclinical mastitis must be done in the dry period. Consequently, during the period between establishment of infection and drying off the infected cow is a threat to her neighbors.

Peptide antimicrobial agents offer a potential solution to many of these problems. The fact that they are peptides means they will be digested by the consumer and this gives them a non toxic profile with regard to warm-blooded animals. A large number of antimicrobial peptides exhibiting a broad activity spectrum is described in the literature but this does not mean that they really can be used to control bovine mastitis.

Lanthionine containing peptides represent an interesting group of antimicrobials because they exhibit a broad spectrum of activity against bacterial pathogens. Typical representatives are Subtilin, Cinamycin, Nisin, Duramycin, Ancovenin, Ro 09-0198, pep5, Lacticin 481, Gallidermin and Epidermin. Some of these peptides are highly active against the bacteria causing bovine mastitis. Several lanthionine containing peptides, most notably nisin, are already used as preservatives in the food industry and in cosmetic preparations.

Thus, these agents could in principle be used in mastitis treatment and any residues remaining in the milk would pose no risk to human health.

However, there remains a severe problem, namely that of cheese and yoghurt manufacture. These processes are based on bacterial fermentation of milk and therefore agents with antimicrobial properties risk upsetting them.

It has been established (Jung et at., 1992), that there is a significant reduction in the antimicrobial effect of Nisin in the presence of milk [see also Tables 1 and 2], which results in a therapeutic dose being so high that the residue activity to be found in the milk of a treated animal strongly interferes with the ability of those microorganisms involved in the production of cheese and yoghurt to accomplish acidification of milk.

It was, therefore, a long felt need to find an antibiotic peptide that fully controls bovine mastitis, is non toxic to warm-blooded animals and does not affect bacteria in milk that play a role in cheese and yoghurt production.

It has now surprisingly been found within the scope of the present invention, that within the group of lanthionine containing peptides two closely related species exist that do not exhibit the mentioned disadvantages of other members of this group. These two representatives are Gallidermin and the structurally very similar Epidermin. The said compounds and their pharmaceutically acceptable acid addition salts have proven not only to be highly active against pathogens causing bovine mastitis but also not to be inhibited in their antipathogenic activity by the presence of milk. What is most important, this lack of inhibition in the presence of milk makes it possible to considerably reduce the therapeutic dose of Gallidermin and Epidermin or their pharmaceutically acceptable acid addition salts, so that problems with regard to the utilization of milk from treated cows in cheese and yoghurt production due to residues are significantly reduced. It was not expected to find within the lanthionine containing peptides representatives which exhibit the above-mentioned advantages over other members of the same class of peptides. The efficacy of Gallidermin and Epidermin in the treatment of mastitis has not heretofore been studied to applicants' knowledge.

Gallidermin is a natural product produced by the microorganism *Staphylococcus gallinarum* and has the following chemical structure:

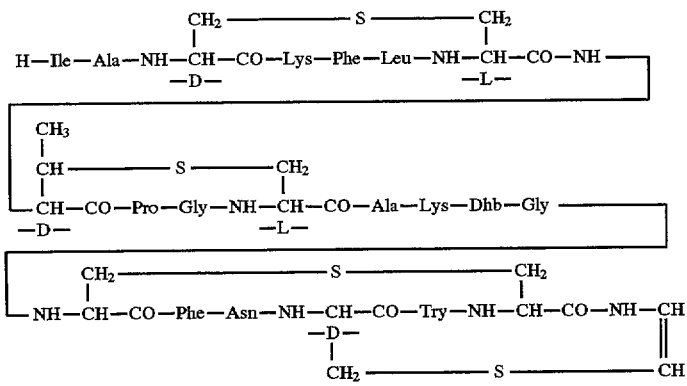

Gallidermin, its structure, its production and its use in pharmaceuticals for treating skin bacterial infections such as eczema, impetigo, cellulitis and acne is described in the European patent application EP-0'342'486. Epidermin is a natural product produced by the microorganism *Staphylococcus epidermis* and has the following chemical structure:

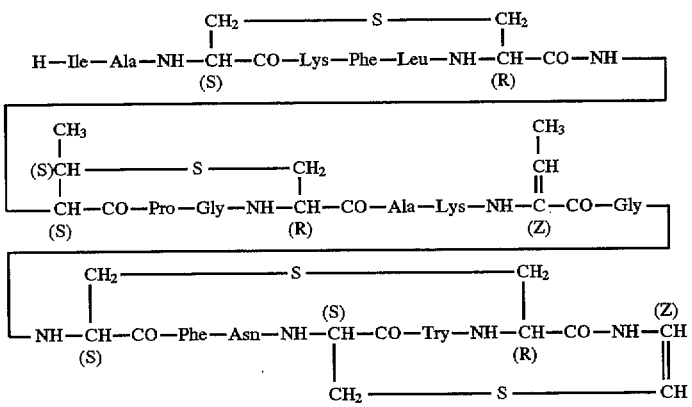

Epidermin, its structure, its production and its use as an antibacterial agent against infections caused by gram positive bacteria is described and claimed in the European patent application EP-0'181'578.

The present invention is based on the surprising finding that Gallidermin and Epidermin and their pharmaceutically acceptable acid addition salts can be used to prevent or treat mastitis in dairy cattle without causing problems with regard to the utilization of the milk in cheese and yoghurt production comparable to those, which are to be observed when using one or more of the conventionally employed antibiotics such as those given in table 4 or even other members of the group of the Lanthionine containing peptides, such as, for example, nisin and lacticin 481. The antimicrobial activity of the latter compounds is strongly inhibited by the presence of milk, which results in therapeutic doses up to 30 times higher than that to be applied when using the compounds according to the invention or the pharmaceutically acceptable acid addition salts thereof.

The advantages of the compounds according to the invention are even more pronounced if they are compared with those antibiotics that are conventionally employed in the treatment of mastitis in dairy cattle such as those given in Table 6, which are applied in doses up to 300 times higher than that for gallidermin and epidermin, respectively. The very low dosage requirements of the compounds according to the invention as compared to the conventionally employed antibiotics and their non toxic profile with regard to warm-blooded animals owing to their peptide nature render them readily acceptable for the consumer.

In one embodiment the present invention is directed to a method of treating or preventing mastitis in a mammal comprising administering to said mammal a therapeutically effective amount of Gallidermin and/or Epidermin or one of their pharmaceutically acceptable acid salts.

In a preferred embodiment the present invention is directed to a method of treating mastitis in a mammal comprising administering to said mammal a therapeutically effective amount of Gallidermin and/or Epidermin or one of their pharmaceutically acceptable acid salts. Most preferred is Gallidermin.

In another embodiment, the instant invention is directed to a method for treating or preventing mastitis in a cow comprising administering to said cow a therapeutically effective amount of Gallidermin and/or Epidermin that may be obtained from a natural source, by chemical synthesis or by means of recombinant DNA technology. The administration can be done either before or after infection.

These and other embodiments of the present invention will readily occur to those of ordinary skill in the an in view of the disclosure herein.

Thus, the main aspect of the present invention is the treatment or prevention of mastitis in mammals by the administration of Gallidermin and/or Epidermin or one of their pharmaceutically acceptable acid salts to the subject mammal. A preferred embodiment of the invention is the treatment or prevention of mastitis in cattle using Gallidermin and/or Epidermin or one of their pharmaceutically acceptable acid salts.

The present invention contemplates employing any form of Gallidermin or Epidermin or one of their pharmaceutically acceptable acid salts, either alone or in combination. Thus, the present invention encompasses using native forms of the active agents. Since the production of recombinant peptides has substantial advantages relative to the purification of native peptides, recombinant peptides are a preferred embodiment. It is also contemplated that synthetic forms of Gallidermin or Epidermin and muteins showing minor structural differences to the native products exhibiting essentially the same biological activity, are also within the scope of the invention.

As indicated, the present invention is concerned with treating or preventing mastitis. By "treating" is meant curing or ameliorating an animal that has contracted mastitis. "Preventing" mastitis means preventing the occurrence of the infection, or tempering the severity of the infection if it is later contracted.

The active agents of the present invention are usually prepared and stored as ready-to-use liquid formulations. The aqueous solution is generally applicable, but the formulation can also be adapted to the specific type of administration. The Gallidermin or Epidermin formulation can also contain non-ionic surfactants that carry no discrete charge when dissolved in aqueous media and are selected from ethoxylated esters of fatty acids and triglycerides. The Gallidermin or Epidermin formulation may also contain EDTA to improve the antimicrobial spectrum and stabilizing agents such as methionines, ascorbic acid, and preservatives such as propylene glycol.

Typically, the active agents of the present invention are administered by intramammary injection; however, effective dosages may be administered parenterally, percutaneously, by implant and also by dipping. In a preferred embodiment of the present invention the administration is carried out via intramuscular, subcutaneous, or intravenous injection. When prepared as injectables, the active agents according to the present invention are generally administered using a pharmaceutically acceptable vehicle or excipient. Suitable vehicles are, for example, water, saline, mannitol, dextran, amino acids, glycerol, or the like, in various combinations. In addition, if desired, the vehicle may contain auxiliary substances such as wetting or emulsifying agents, preservatives and pH buffering agents. The active ingredient will typically range from about 1% to about 95% (w/w) of the composition administered, or even higher or lower if appropriate.

Parenteral administration may be conventionally accomplished by subcutaneous, intradermal, intramuscular, and even intravenous injection. Needle-less air-blast injection devices may be equally useful. Parenteral administration is well known in the art and may be carried out in ways common in the animal veterinary or human medical art.

Sustained action of the active agent to achieve prolonged release (so called 'slow release') can be obtained by formulating the protein in a matrix that will physically inhibit rapid dissolution. The formulated matrix is injected into the animal's body where it remains as a depot from which the protein is slowly released. Useful adjuvants in this respect are polymers and copolymers of lactides and glycosides. Furthermore, gelling agents like aluminum, calcium or magnesium monostearate, or carbohydrates (cellulose, pectin, dextran derivatives), polysiloxanes or proteins (gelatin, collagen) may be used to extend the releasing time of the active agents of the present invention after parenteral application. Percutaneous administration is also meant to include implantation of controlled release devices, e.g. made from silicone or wax and other implantable matrices from polymeric materials can be used subcutaneously to deliver the compound over the required period of time. This can also be achieved by implantation of minipumps containing aqueous solutions of the protein. Such implantation techniques are also well known in the art and often used in medical treatment.

Polysiloxane carriers are described in the an for a variety of hormonal delivery forms and may be adapted to the release of the active agents of the present invention. A collagen delivery system for the release of antibiotics is described in the German Offenlegungsschrift DE-3,429,038. This system can also be adapted for Gallidermin or Epidermin delivery.

Slow release formulations and other pharmaceutical or veterinary Gallidermin or Epidermin formulations can be prepared by adapting, for example, the Gallidermin or Epidermin formulation or other protein formulations already described in the art.

A "therapeutically effective amount" of an active agent of the present invention is a dose sufficient to either prevent or treat mastitis in a subject to which the active agent is administered. The dosages of the active agents of the present invention which can treat or prevent mastitis can be determined in view of this disclosure by one of ordinary skill in the art by running routine trials with appropriate controls. Comparison of the appropriate treatment groups to the controls will indicate whether a particular dosage is effective in preventing or treating a disease used in a controlled challenge. In general, effective dosage will vary depending on the mode of administration. It has been found that in the case of an intramammary injection using Gallidermin and Epidermin administration of a dose in the range of from 0.1 mg per quarter to 10 mg per quarter, preferably of from 0.5 mg per quarter to 5 mg per quarter, more preferably of from 1 mg per quarter to 3 mg per quarter and most preferable of 1 mg per quarter is sufficient to control mastitis due to *Staphylococcus aureus*.

If administered intramuscularly, subcutaneously, or intravenously, effective dosages will depend on the weight of the animal and will typically run in the range of from about 20 µg/kg to about 200 µg/kg. More typically, the dosage will be at least about 50 µµg/kg, but less than 150 µg/kg.

Beyond dosage, an effective administration of an active agent according to the present invention will in part depend on the number and timing of the dosages. For example, multiple administrations of a dosage may be given to an animal, typically at least about 12 hours apart. In most circumstances it may be desirable to administer the active agent at least three times. It may even be desirable to administer even more dosages to the animal, such as six, seven, eight, or even nine over an equal number of days or longer. Again, it is believed that the precise combination of dosage and timing will be subject to a wide range of variation and that numerous combinations effective in treating or preventing a disease can be readily established by those of ordinary skill in the art in view of the present disclosure.

The active agents of the subject invention can be administered prior to infection, and thus serve as a prophylactic or can be given after the subject has shown signs of infection.

Described below are several examples illustrating the practice of the present invention. These examples are provided for illustrative purposes only, and are not intended to limit the scope of the appended claims.

EXPERIMENTAL

MIC plate assay

The MICs (Minimal Inhibitory Concentrations) of Gallidermin against *Streptococcus aureus* and *Streptococcus diacetylactis* were determined. *S. aureus* Newbold 305 is a causative agent of Mastitis, *S. diacetylactis* is used in the manufacture of yoghurt and cheese.

Appropriate dilutions Gallidermin (300, 100, 30, 10, 3, 1, 0.3, 0.1 mug/ml) were prepared in milk and in M17 broth (Merck) and allowed to stand at room temperature for 30 min.

Then, 10 ml aliquots of the solutions were spotted on M17 agar plates containing 0.5% of glucose. These plates had been overlaid with softagar (0.5% agarose) seeded with 1% of an A600=1 culture of either *S. aureus* or *S. diacetylactis*. The spots were allowed to dry, then the plates were incubated at 30° C. overnight.

The MICs were determined as the lowest concentration of antimicrobial protein causing the formation of a clear halo in the bacterial lawn. The results presented in table 1 show that Gallidermin has comparable activities against *Streptococcus diacetylactis*, both in milk and broth.

TABLE 1

| MICs of Gallidermin (mug/ml) | | milk | M17 |
| --- | --- | --- | --- |
| Gallidermin | S. aureus | 0.3 | 1 |
|  | S. diacetylactis | 1 | 0.3 |

Effect of Gallidermin on *Streptococcus aureus* in milk

*Staphylococcus aureus* Newbold 305 was grown in M17 broth (Merck) at 37° C. to an optical density at 600 nm of 1.0. Cells were collected by centrifugation and washed in 20 mM Tris-HCl pH 8.0. The bacterial pellet was resuspended in milk at a density of about $10^7$ cells/ml.

1 ml aliquots of this suspension were incubated in eppendorf tubes with various amounts of Nisin, Lacticin 481 and Gallidermin. Incubations were at 37° C. for 30 min. A control with no antimicrobial added was run in parallel.

After incubation the samples were centrifuged to obtain the cellular pellet, which was washed 2 times with 1 ml of 20 mM Tris-HCl pH 8.0 and resuspended in 1 ml of this buffer. 100 ml of the appropriate dilutions were plated on M17 agar plates containing 0.5% glucose and incubated overnight at 37° C. Colony forming units (cfu) were determined and percent survival was calculated relative to the control.

The results are shown in table 2. It is clear from these data that in milk Gallidermin retains a high specific activity against *Staphylococcus aureus*, whereas acitivty of both Nisin and Lacticin 481 is strongly inhibited in the presence of milk.

TABLE 2

Effect of Nisin, Lacticin 481 and Gallidermin on *S. aureus* in milk.

| conc mug/ml | % survival | | |
| --- | --- | --- | --- |
|  | Nisin | Lacticin 481 | Gallidermin |
| 100 | 0.2 | 12 |  |
| 30 | 1.8 | 30 |  |
| 10 | 15 | 36 | 0.01 |
| 3 | 65 | 51 | 1 |
| 1 |  | 74 | 12 |
| 0.3 |  |  | 29 |
| contr. | 100 |  | 100 |

It is well documented that Nisin is inhibited in the presence of milk (Jung et al., 1992). Clearly and surprisingly Gallidermin does not show a similar inhibition in the presence of milk. It is this particular property that suits it so well for use as a prophylactic and therapeutic agent for use in bovine mastitis since the therapeutic dose can be lowered accordingly.

To evaluate the potential of Gallidermin, Epidermin or of their pharmaceutically acceptable acid addition salts in subclinical bovine mastitis caused by *Staphylococcus aureus* the infection model described below can be used.

EXAMPLE 1

Preliminary experiments for evaluating the potential of Gallidermin, Epidermin or of their pharmaceutically acceptable acid addition salts in subclinical bovine mastitis Non-infected cows are selected based on non recovery of *Staphylococcus aureus* from two milk samples taken one day apart from all quarters. Then, 3 quarters are inoculated via the intramammary route using a suspension of *Staphylococcus aureus*. The 4th quarter serves as control. During the two to four weeks after inoculation, milk samples are taken from all quarters at least 3 times to see whether *Staphylococcus aureus* can be recovered, and therefore whether the quarter has become infected. A quarter is defined as infected, if *Staphylococcus aureus* is recovered from at least two of these milk samples. Treatments are assigned randomly to infected quarters and injected via the intramammary route. Milk samples are taken daily until a minimum of 14 days after the last treatment. A quarter is considered as cured if milk samples from that quarter become negative (i.e., no *Staphylococcus aureus* is recovered) within 7 days after the last treatment and stay negative throughout the 14 day sampling period.

This experimental model is used to have a fixed framework on which to evaluate treatments. To work with *Staphylococcus aureus* has the advantage that it is the most difficult Gram positive bacterium to treat and one of the most important bacteria causing bovine mastitis. Therefore, cure rates should be expected to be lower than for other Gram positive bacteria, such as Streptococci and coagulase-negative Staphylococci.

This model has proved satisfactory since the infection rate in quarters averaged 60%, or 2 quarters/cow. In addition, the infection is mild as it should be for subclinical mastitis.

To optimize work load in relation to man power, 8 to 16 cows are enrolled in each trial. Trials normally last 5 weeks.

HERD MANAGEMENT

We maintain a dairy herd, to supply candidate cows for enrollment in trials.

Cows are bought from local cattle dealers. These cows should have a minimal milk production of 15 l/day. Two milk samples are taken one day apart from all quarters for bacteriological examination. No cow from which mastitis pathogens can be recovered are entered into tests.

TABLE 3

Summary of in vitro results
The results provided in Table 3 show the percent of quarters positive from different treatment groups during treatment and for 14 days after the end of treatment.

| treatment group day | gallidermin 3 × 1 mg % of treated group positive (27 qutrs) | ampiclox 3 × 300 mg ampiclox doses (68 qurts) | short treatment control % of control group positive (45 qutrs) | long treatment control % of control group positive (13 qutrs) | gallidermin 14 × 0.1 mg % of treated group positive (24 qutrs) |
|---|---|---|---|---|---|
| 0 | 93 | 100 | 97.7 | 92 | 96 |
| 1# | 37 | 19 | 75.6 | 92 | 88 |
| 2* | 11 | 1 | 77.8 | 77 | 88 |
| 3 | 26 | 7 | 80 | 92 | 71 |
| 4 | 56 | 6 | 73.3 | 77 | 58 |
| 5 | 59 | 24 | 77.8 | 69 | 67 |
| 7** | 56 | 29 | 75.6 | 77 | 50 |
| 8 | 56 | 34 | 75.6 | 77 | 67 |
| 9 | 52 | 35 | 71.1 | 85 | 71 |
| 10 | 56 | 35 | 75.6 | 62 | 88 |
| 11 | 56 | 43 | 71.1 | 62 | 83 |
| 12 | 52 | 41 | 64.4 | 69 | 88 |
| 14 | 48 | 43 | 68.9 | 77 | 79 |
| 15 | 52 | 43 | 80 | 69 | 88 |
| 16 | | | 80 | 85 | 83 |
| 17 | | | | 85 | 83 |
| 19 | | | | 77 | 79 |
| 21 | | | | 69 | 83 |

For all treatment groups treatment starts at day 1
*Treatment ends after day 2 for the gallidermin (3 × 1 mg), the ampiclox (3 × 300 mg) and the short treatment control groups.
**Treatment ends after day 7 for the gallidermin (14 × 0.1 mg) and the long treatment control group, respectively.

TEAT DIPPING AND MASTITIS PROPHYLAXIS

Teat clipping is one of the most frequently used and most effective measures taken to prevent mastitis in dairy cows. This widely practiced procedure involves dipping the 4 teat of every cow, after every milking, in an antibacterial solution. This procedure leaves a coating of antibacterial substances on the teat surface and a droplet of this substance collects at the dependent part of the teat over the teat orifice. After milking a droplet of milk often covers the teat orifice and is a good medium for bacterial growth. From this position the bacteria can readily penetrate the streak canal. Teat dipping provides protection against these possibilities.

In some herd, teats are dipped before milking to kill off any pathogens resident on the teat surface before the milking machine is applied. To be useful as a pre-milking teat dip, agents need to be non-toxic and non-disruptive to cheese and yoghurt manufacture.

Products currently used for teat dipping contain a variety of different active ingredients such as iodophors, chlorhexidiene and the lanthionine containing peptide, nisin.

Gallidermin and Epidermin and their pharmaceutically acceptable acid additional salts are very suitable for use in teat dips because of their rapid killing effect and preferential activity against major mastitis pathogens. Rapid killing gives a special application as an agent for pre-dipping.

Teat dip protocol

To evaluate the potential of Gallidermin and Epidermin and their pharmaceutically acceptable acid addition salts as prophylactic agents in bovine mastitis, the following experimental protocol can be used.

Experimental animals: 50 cattle are recruited according to the protocol already described for trials of these agents in therapy of subclinical staphylococcal mastitis. This trial then proceeds according to protocol recognised by the US National Mastitis Council (NMC) (Hogan et al. 1990) for testing efficacy of teat germicides during experimental exposure.

Throughout the trial period all teats are dipped in a challenge bacterial suspension containing $15 \times 10^7$ Streptococcus aureus and $5 \times 10^7$ Streptococcus agalactiae after the evening milking on week days. Challenge suspensions are prepared daily from stock solutions that are made up weekly. Aliquots of challenge solution are plated each day to determine the real bacterial concentration present at the time of challenge.

After each milking the left fore and right hind quarters are dipped in the test preparation of germicide, the other two teats remain as negative controls and are not dipped. Routine foremilk samples of all quarters are taken twice per week throughout the trial, for bacteriological examination. Any quarter, from which either challenge organism is isolated, is resampled within 48 hours of the original sample. If the same organism is isolated then the quarter is considered infected. Similarly an episode of clinical mastitis caused by either challenge organism is considered as a new intramammary infection (IMI).

At the end of the trial period the number of new intramammary infection between treatment groups is compared.

GALLIDERMIN AND EPIDERMIN IN CHEESE AND YOGHURT

To evaluate the potential effects of Gallidermin and Epidermin or their pharmaceutically acceptable acid additional salts on strains of bacteria used in cheese and yoghurt manufacture the following experiments can be performed.

Experiment 1

Evaluation of kinetics of reaction of Delvotest P in milk from quarters treated with Gallidermin, Epidermin or their pharmaceutically acceptable acid addition salts.

Background information

Delvotest P is a commercially available, widely used, kit for detection of antimicrobial agents in milk. It relies on inhibition of the growth of Bacillus stearothermophilus. The indicator bacteria are suspended in an agar plug in a plastic test tube together with a pH indicator. Growth of bacteria results in acid production and colour change. In the presence of inhibiting substances the bacteria do not grow and there is no colour change. Bacillus stearothermophilus is a good representative of bacteria used in cheese and yoghurt manufacture and hence it is widely used as the indicator strain in antibiotic residue detection.

Experimental method

This experiment is performed at the same time and on the same animals, as the efficacy and kinetic trials. During the period following administration of various treatments samples are taken at morning and evening milkings. These samples are evaluated using Delvotest P as directed in the manufacturers recommendations. This twice daily sampling goes on until all treated quarters show a negative response. In this way the duration of elimination of the antibacterial agent can be established.

TABLE 4

Results of Delvotest P in milk from bovine mammary gland quarters treated with different concentrations of gallidermin and with Nisin.

| Agent used | dose [mg] | No of quarter treated | treatment regime | no of milkings after last treatment that Delvtest P pos or +/- |
|---|---|---|---|---|
| gallidermin | 0 | 12 | 3 at 12 hrs | 0 |
| gallidermin | 0.1 | 4 | 3 at 12 hrs | 0 |
| gallidermin | 0.5 | 4 | 3 at 12 hrs | 1 |
| gallidermin | 1 | 12 | 3 at 12 hrs | 2 |
| gallidermin | 2 | 8 | 3 at 12 hrs | 2 |
| gallidermin | 5 | 8 | 3 at 12 hrs | 3 |
| gallidermin | 30 | 38 | 3 at 12 hrs | 8* |

*all but 2 of 38 treated quarters were negative at 96 hrs after the last treatment

Experiment 2

Evaluation of effects of various concentrations of Gallidermin, Epidermin or their pharmaceutically acceptable acid additional salts on acidification of milk by cheese starter bacteria In cheese and yoghurt manufacture different strains of bacteria are fermented in milk and one of the most important and immediate changes resulting from this fermentation is acid production. This acid is responsible for the control of secondary bacterial growth that could cause spoilage of the product or worse, illness in the consumer. Further fermentation of the lactic acid producing bacterial population produces changes in the cheese that vary with the strains of the bacteria used and the manufacturing methods. These factors are responsible for the physical characteristics and the flavour of different cheeses.

Acidification is the first and most important step in the manufacturing processes when milk is fermented. If acidification proceeds normally then it is very likely that all other steps will be normal. Therefore one can investigate the ability of different concentrations of Gallidermin, Epidermin or their pharmaceutically acceptable acid addition salts on the kinetics of acidification of milk by different bacterial strains used in these manufacturing processes.

Protocol

Experiments are routinely performed using one of three strains of bacteria

*Streptococcus thermophilus*
*Lactobacillus bulgaricus*
*Lactococcus lactis-cremoris*

Preparation of stock cultures

Lyophylised cultures as used in commercial conditions are obtained from Rudolf Wittwer, CH-5002 Rombach, Aarau, Switzerland. These cultures are reconstituted according to manufacturers recommendations and reactivated by passage three times in sterile skimmed milk. Each passage is incubated for 16-18 hours at the optimum temperature for each bacterial strain.

The culture obtained after the third passage is diluted to 2% with whole sterile (UHT) milk, aliquotted in 10 ml tubes and frozen at -20° C. for use in experiments.

Preparation of experimental culture

The stock cultures prepared above are thawed at 40° C. then incubated overnight at 37° C. and used to inoculate test samples at a concentration of 2% in whole sterile (UHT) milk.

Preparation of test samples

The antimicrobial agent under test (Gallidermin, Epidermin or one of their pharmaceutically acceptable acid addition salts) is diluted in sterile (UHT) whole milk over the required dilution range. These samples are then inoculated with 2% by volume of the experimental culture of the strain of bacteria being tested. The samples are then mixed and incubated at optimal temperature for the bacterial strain under evaluation. The pH is measured each two hours for a period of eight hours and then at 18 hours after inoculation. The rate of acidification of milk containing different concentrations of active ingredients can then be compared to the rate without any active ingredient.

Experiment 3

Evaluation of the direct effect on yoghurt manufacture of treatment of mammary gland quarters with different doses of antimicrobial agents Cows that are free from infection with mastitis pathogens, based on bacteriological culture of milk, are enrolled in these trials. Identical treatments are administered to all 4 quarters of an individual cow. The milk from each milking from each cow is then kept separate and used in the experiment. Milk from evening milkings is refrigerated at 4° C. overnight to be used the following morning. Samples of 500 ml of the evening milking and also those from the morning are heated to 80° C. in a waterbath and then cooled to room temperature. Inoculation with culture bacteria, incubation and measurement of pH then proceed as described previously.

TABLE 5

Witholding time (the time between last treatment and lack of effect on acidification of milk by dairy starter cultures) after treatment with various amounts of gallidermin.

| bacterial strain | substance | frequency of application | number of applications | dose | witholding time |
|---|---|---|---|---|---|
| Lacto- | galli- | 12 hrs | 3 | 1 mg | 24-36 h |
| bacillus | dermin | 12 hrs | 3 | 2 mg | >36 h |
| bulgaricus | | 12 hrs | 3 | 5 mg | >36 h |
| Strep. | galli- | 12 hrs | 3 | 5 mg | >36 h |
| thermo- | dermin | 12 hrs | 3 | 1 mg | 24-36 h |
| philus | | 12 hrs | 3 | 2 mg | 36 h |
| Lacto- | galli- | 12 hrs | 3 | 0.5 mg | 36 h |
| bacillus | dermin | 12 hrs | 3 | 0.1 mg | 0 h |
| bulgaricus | | 12 hrs | 3 | 1 mg | 24-36 h |
| Strep. | galli- | 12 hrs | 3 | 0.5 mg | 36 h |
| thermo- | dermin | 12 hrs | 3 | 0.1 mg | 0 h |
| philus | | 12 hrs | 3 | 1 mg | 24-36 h |

The witholding times of some of the commonly employed antibiotics in the treatment of mastitis are given in the following table 6.

TABLE 6

Antibiotics commercially employed in the treatment of mastitis in dairy cattle

| | | Witholding Time | |
|---|---|---|---|
| Product | Company | hours | milkings |
| Ampiclox | SBAH | 48-72 | 4-6 |
| Kloxerate plus | Solvay Duphar | 60 | 5 |
| Mastijet | Intervet | 96 | 8 |
| Tetra delta | Upjohn | 72 | 6 |
| Synulox | SBAH | 48 | 4 |

REFERENCES

Hogan, J. S., Galton, D. M., Harmon, R., Nickerson, S. C., Oliver, S. P., Pankey, J. W. (1990) Protocols for Evaluating efficacy of postmilking teat dips. J. Dairy Sci. 73 pp 2580–2585.

Jung, D. S., Bodyfelt, F. W., and Daeschel, M. A., (1992) Influence of fat and emulsifires on the efficacy of nisin in inhibiting Lysteria monocytogenis in fluid milk. J. Dairy Science 75 pp 387–393.

Philpot, W. N., (1984) Economics of mastitis control, Veterinary Clinics of North America: Large Animal Practice 6(2) pp 233–245.

Cullor, J. S., Tyler, J. W., Smith, B. P. (1990) Disorders of the mammary gland in large animal medicine, B. P. Smith, The C. V. Mosby Company, St Louis, Mo. 63146, USA., pp 1047–1067.

We claim:

1. A method for combatting bacterial mammary mastitis in a mammal which method permits milk obtained from the mammal to be used in the production of cheese or yogurt, said method comprising administering to said mammal a composition comprising from about 20 µg/kg to 200 µg/kg of gallidermin, or a pharmaceutically acceptable acid salt thereof.

2. The method according to claim 1 wherein the active agent is of native, recombinant or synthetic origin, or is a mutein thereof, exhibiting activity against mastitis in a mammal.

3. The method of claim 1 wherein said mammal is a cow, goat or ewe.

4. The method of claim 1 wherein the active agent is administered via intramammary injection or by or dipping the teat.

5. The method of claim 3 wherein the mammal is a cow and wherein said administration is achieved by intramammary injection of the therapeutically effective amount of gallidermin or a pharmaceutically acceptable acid salt thereof during the prepartum period.

6. The method of claim 3 wherein the mammal is a cow and said intramammary injection of gallidermin or a pharmaceutically acceptable acid salt thereof after the onset of infection.

7. The method of claim 6 wherein said injection is given during the postpartum period.

8. A method for combatting bacterial mammary mastitis in a mammal which method comprises, of milk obtained from mammals suffering from mastitis for the production of cheese administering to said mammal from about 20 µg/kg to 200 µg/kg of gallidermin, or a pharmaceutically acceptable acid salt thereof yet permitting milk obtained after administration of said gallidermin to be used in the production of cheese or yogurt.

* * * * *